United States Patent [19]
Wernthaler et al.

[11] Patent Number: 6,100,288
[45] Date of Patent: Aug. 8, 2000

[54] ACYLATED 5-AMINOPYRAZOLES AND THE USE THEREOF TO COMBAT ANIMAL PARASITES

[75] Inventors: Konrad Wernthaler, Kienberg; Markus Heil, Leverkusen; Christoph Erdelen, Leichlingen, all of Germany

[73] Assignee: Bayer Aktiengesellschaft, Leverkusen, Germany

[21] Appl. No.: 09/300,508

[22] Filed: Apr. 28, 1999

Related U.S. Application Data

[62] Division of application No. 09/145,532, Sep. 2, 1998, Pat. No. 5,981,566, which is a division of application No. 08/875,060, filed as application No. PCT/EP95/05148, Dec. 28, 1995, Pat. No. 5,843,978.

[30] Foreign Application Priority Data

Jan. 13, 1995 [DE] Germany .................. 195 00 789

[51] Int. Cl.⁷ .................. A01N 43/56; C07D 231/40
[52] U.S. Cl. .................. 514/404; 548/371.7; 548/372.5
[58] Field of Search .................. 548/371.7, 372.5; 514/404

[56] References Cited

U.S. PATENT DOCUMENTS 5,556,873  9/1996  Huang et al. .
5,656,629  8/1997  Baron et al. .................. 514/234.5

FOREIGN PATENT DOCUMENTS 257 479  3/1988  European Pat. Off. .
289 879  11/1988  European Pat. Off. .

OTHER PUBLICATIONS

Wernthaler, Chemical Abstracts, vol. 125, No. 167,977 1996.
Kato et al, Chemical Abstracts, vol. 107, No. 198317 1987.
Chemical Abstracts, vol. 110, No. 11, (Mar. 13, 1989) Columbus, Ohio U.S., Abstract No. 90608w, S. Kato et al., Fruit Thinning Agents Containing Pyrazoles, p. 275, Col. 2 & JP, A,63 174 905 (Tokuyama Soda Co., Ltd.), Jul. 19, 1988.
Chemical Abstracts, vol. 107, No. 19 (Nov. 9, 1987), Columbus, Ohio, U.S., Abstract No. 176028g, S. Kato et al. Preparation of [(phenoxyalkanoyl)amino]pyrazole derivatives as herbicides, fungicides and bactericides, p. 725, Abstracts, Chemical Substances, 12th Collective Index, vol. 106–115,. 1987–1991, Col. 2 & JP, A,62 138 475 (Tokuyama Soda Co., Ltd.) Jun. 22, 1987.
Chemical Abstracts, vol. 111, No. 15, (Oct. 9, 1989) Columbus, Ohio, U.S., Abstract No. 134141r, S. Kato et al., Preparation of [(phenoxy– or 2–pyridyloxalkylacyl)amino] pyrazole derivatives as herbicides and microbicides, p. 761, Col. 2; Abstracts, Chemical Substances, 12th Collective Index, vol. 106–115, 1987–1991 & JP,A,63 313 773 ((Tokuyama Soda Co., Ltd.), Dec. 21, 1988.
Chemical Abstracts, vol. 120, No. 23 (Jun. 6, 1994) Columbus, Ohio, U.S., Abstract No. 298596e, C.B. Vincentini et al. "An Efficient Procedure for the Synthesis of pyrazolo[3,4–d][1,3] thiazin–4–ones", p. 978, Col. 2; Abstracts, Chemical Substance Index, vol. 120 (1994) & Heterocycles, vol. 36, No. 10 (1993) Amsterdam NL, pp. 2291–2301.
Chemical Abstracts, vol. 116, No. 7 (Feb. 17, 1992) Columbus, Ohio, U.S., Abstract No. 53692x, S. Kato et al. Preparation of Pyrazoles for Fruit Abscission Inhibition and Color Enhancement of Apples:, p. 316, Col. 1; Abstracts, Chemical Substance Index, vol. 116 (1992) & JP,A,03 173 806 (Tokuyama Soda Co., Ltd.) Jul. 29, 1991.
Chemical Abstracts, vol. 119, No. 3 (Jul. 19, 1993), Columbus, Ohio, U.S., Abstract No. 28159h, M.M. Fawzi "Preparation of N–aryl –2–2 [4–(6–chloro–2–quinoxalinyloxy)phenoxy]propanamides as herbicides.", p. 878, Col. 1; Abstracts, Chemical Substance Index, vol. 119 (1993) & EP,A,0 527 016 (Du Pont De Nemours, E. I. and Co.) Feb. 10, 1993.
Chemical Abstracts, vol. 113, No. 7 (Aug. 13, 1990) Columbus, Ohio, U.S., Abstract No. 59158n, K. Toyabe et al. "Benzoxazolyloxphenoxypropionic acid derivatives as herbicides and their preparation", p. 703, Col. 1; Abstracts, Chemical Substances, 12th Collective Index, vol. 106–115, 1987–1991 & JP,A,02 017 187 (Kumiai Chemical Industry Co., Ltd.) Jan. 22, 1990.

Primary Examiner—Robert W. Ramsuer
Attorney, Agent, or Firm—Norris, McLaughlin & Marcus, P.A.

[57] ABSTRACT

The present invention relates to new acylated 5-aminopyrazoles of the formula (I)

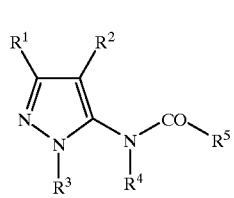

(I)

in which

R¹, R², R³, R⁴ and R⁵ have the meaning given in the description, to processes for their preparation and to their use as pesticides.

8 Claims, No Drawings

ACYLATED 5-AMINOPYRAZOLES AND THE USE THEREOF TO COMBAT ANIMAL PARASITES

This application is a divisional of Application Ser. No. 09/145,532, filed Sep. 2, 1998 (now U.S. Pat. No. 5,981, 566), which is a division of Ser. No. 08/875,060, filed Jul. 7, 1997 (now U.S. Pat. No. 5,843,978), which is a 371 of PCT/EP95/05148, filed Dec. 28, 1995.

The present invention relates to new acylated 5-aminopyrazoles, to processes for their preparation, and to their use for controlling animal pests, in particular insects, arachnids and nematodes found in agriculture, in forests, in the protection of stored products and of materials, and in the hygiene sector.

It has already been disclosed that certain 1-aryl-5-aminopyrazole derivatives (cf., for example, EP-A 0 257 479 and EP-A 0 243 636) have insecticidal and acaricidal properties.

However, efficacy and spectrum of action of these compounds is not always entirely satisfactory, in particular when low rates and concentrations are applied.

There has now been found new acylated 5-aminopyrazoles of the formula (I)

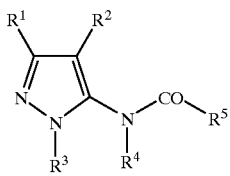

(I)

in which
$R^1$ represents alkyl, alkoxyalkyl or halogenoalkyl,
$R^2$ represents hydrogen, halogen, cyano, nitro, halogenoalkylthio, alkoxycarbonyl or alkenyloxycarbonyl,
$R^3$ represents alkyl or optionally substituted cycloalkyl,
$R^4$ represents hydrogen, alkyl or optionally substituted cycloalkyl and
$R^5$ represents the group —Y—$R^6$, where
   Y represents optionally substituted alkanediyl and
   $R^6$ represents in each case optionally substituted aryl or aryloxy.

Furthermore, it has been found that the acylated 5-aminopyrazoles of the formula (I) are obtained when
a) 5-aminopyrazoles of the formula (II)

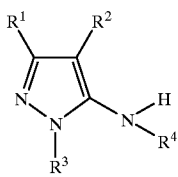

(II)

in which
$R^1$, $R^2$, $R^3$ and $R^4$ have the abovementioned meaning are reacted with acid halides of the formula (III)

$R^5$—CO—Hal (III)

in which
$R^5$ has the abovementioned meaning and
Hal represents halogen
in the presence of a base and in the presence of a diluent;
or
b) acylated 5-aminopyrazoles of the formula (Ia)

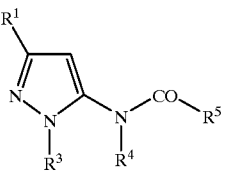

(Ia)

in which
$R^1$, $R^3$, $R^4$ and $R^5$ have the abovementioned meaning are reacted
  (α) with a halogenating agent, if appropriate in the presence of a diluent and if appropriate in the presence of a catalyst,
or
  (β) with a nitrating agent, if appropriate in the presence of a diluent.

Finally, it has been found that the new acylated 5-aminopyrazoles of the formula (I) have pronounced biological properties and are suitable, above all, for controlling animal pests, in particular insects, arachnids and nematodes, which are found in agriculture, in forests, in the protection of stored products and of materials, and in the hygiene sector.

Formula (I) provides a general definition of the acylated 5-aminiopyrazoles according to the invention.

Preferred substituents or ranges of the radicals given in the formulae mentioned hereinabove and hereinbelow are illustrated in the following text.

$R^1$ preferably represents $C_1$–$C_4$-alkyl, $C_1$–$C_4$-alkoxy or $C_1$–$C_4$-alkyl or $C_1$–$C_4$-halogenoalkyl.

$R^2$ preferably represents hydrogen, halogen, cyano, nitro, trifluoromethylthio, difluoromethylthio, $C_1$–$C_4$-alkoxycarbonyl or $C_2$–$C_4$-alkenyloxycarbonyl.

$R^3$ preferably represents $C_1$–$C_4$-alkyl, or represents $C_3$–$C_6$-cycloalkyl which is optionally substituted by halogen or $C_1$–$C_4$-alkyl.

$R^4$ preferably represents hydrogen, $C_1$–$C_4$-alkyl, or represents $C_3$–$C_6$-cycloalkyl which is optionally substituted by halogen or $C_1$–$C_4$-alkyl.

$R^5$ preferably represents the group —Y—$R^6$ where
   Y represents $C_1$–$C_4$-alkanediyl which is optionally substituted by halogen or $C_3$–$C_6$-cycloalkyl.
   $R^6$ preferably represents phenyl or phenoxy, each of which is optionally monosubstituted to trisubstituted by identical or different substituents, suitable substituents being halogen, nitro, cyano, $C_1$–$C_{12}$-alkyl, $C_1$–$C_{12}$-alkoxy, $C_1$–$C_{12}$-alkylthio, $C_1$–$C_{12}$-halogenoalkyl, $C_1$–$C_{12}$-halogenoalkoxy, $C_1$–$C_{12}$-halogenoalkylthio, $C_2$–$C_{12}$-alkenyl, $C_1$–$C_{12}$-alkoxy-$C_2$–$C_{12}$-alkenyl, $C_1$–$C_4$-alkylthio-$C_2$–$C_{12}$-alkenyl, $C_2$–$C_{12}$-halogenoalkenyl, and also phenyl, phenoxy, phenylthio or benzyl, each of which is optionally monosubstituted to trisubstituted by identical or different substituents from the series consisting of halogen, nitro, cyano, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy or $C_1$–$C_4$-halogenoalkylthio.

$R^1$ especially preferably represents methyl, ethyl, n- or i-propyl or n-, i-, s- or t-butyl; or represents methoxymethyl, ethoxymethyl, methoxyethyl, ethoxyethyl, trifluoromethyl, difloromethyl, fluoromethyl, 1-chloro-1-ethyl or 1-fluoro-1 -ethyl.

$R^2$ especially preferably represents hydrogen, fluorine, chlorine, bromine, cyano, nitro, trifluoromethylthio, difluoromethylthio, methoxycarbonyl, ethoxycarbonyl, n- or i-propoxycarbonyl, n-, i-, s- or t-butoxycarbonyl or allyloxycarbonyl.

$R^3$ especially preferably represents methyl, ethyl, n- or i-propyl, n-, i-, s- or t-butyl, or represents cyclopropyl, cyclopentyl or cyclohexyl, each of which is optionally substituted by fluorine, chlorine, methyl and/or ethyl.

$R^4$ especially preferably represents hydrogen, methyl, ethyl, n- or i-propyl, n-, i-, s- or t-butyl, or represents cyclopropyl, cyclopentyl or cyclohexyl, each of which is optionally substituted by fluorine, chlorine, methyl and/or ethyl.

$R^5$ especially preferably represents the group —Y—$R^6$, where

Y represents one of the groups —$CH_2$—, —$CH(CH_3)$—, —$CH_2CH_2$—, —$CH(C_2H_5)$—, —$CH(C_3H_7$—i)—, —CHF—, CHCl— or —CH(cyclopropyl)—.

$R^6$ especially preferably represents phenyl or phenoxy, each of which is optionally monosubstituted to trisubstituted by identical or different substituents, suitable substituents being chlorine, bromine, nitro, cyano, methyl, ethyl, n- and i-propyl, n-, i-, s- and t-butyl, methoxy, ethoxy, n- and i-propoxy, n-, i-, s- and t-butoxy, methylthio, trifluoromethyl, difluoromethyl, trifluoromethoxy, difluoromethoxy, trifluoromethylthio, difluoromethylthio, and also phenyl or phenoxy, each of which is optionally monosubstituted to trisubstituted by identical or different substituents from the series consisting of chlorine, bromine, nitro, cyano, methyl, ethyl, methoxy, ethoxy, n- or i-propoxy or n-, i-, s- or t-butoxy, trifluoromethyl, trifluoromethoxy, difluoromethoxy or trifluoromethylthio.

$R^1$ very especially preferably represents methyl, ethyl, i-propyl, t-butyl, methoxymethyl, 1-chloro-1-ethyl or 1-fluoro-1-ethyl.

$R^2$ very especially preferably represents hydrogen, chlorine, bromine, cyano, nitro, methoxycarbonyl, ethoxycarbonyl, isopropoxycarbonyl or allyloxycarbonyl.

$R^3$ very especially preferably represents methyl, ethyl, i-propyl, t-butyl, or cyclopropyl.

$R^4$ very especially preferably represents hydrogen, methyl, ethyl, i-propyl or cyclopropyl.

$R^5$ very especially preferably represents the group —Y—$R^6$, where

Y represents one of the groups —$CH_2$—, —$CH(CH_3)$— or —$CH_2CH_2$—.

$R^6$ very especially preferably represents phenyl or phenoxy, each of which is optionally monosubstituted or disubstituted by identical or different substituents, suitable substituents being chlorine, bromine, nitro, cyano, methyl, ethyl, n- and i-propyl, n-, i-, s- and t-butyl, methoxy, ethoxy, n- and i-propoxy, n-, i-, s- and t-butoxy, trifluoromethyl, trifluoromethoxy and difluoromethoxy, and also phenyl or phenoxy, each of which is optionally monosubstituted to trisubstituted by identical or different substituents from the series consisting of chlorine, bromine, nitro, cyano, methyl, methoxy, ethoxy, n- or i-propoxy or n-, i-, s- and t-butoxy, trifluoromethyl, trifluoromethoxy, difluoromethoxy or trifluoromethylthio.

The definition of radicals and illustrations given above in general terms or in preferred ranges apply to the end products and, correspondingly, to the starting materials and, intermediates. These definitions of radicals can be combined with each other as desired, that is to say combinations between the respective preferred ranges are also possible.

Preferred compounds of the formula (I) according to the invention are those which contain a combination of the meanings mentioned above as being preferred (preferable).

Especially preferred compounds of the formula (I) according to the invention are those which contain a combination of the meanings mentioned above as being especially preferred.

Very especially preferred compounds of the formula (I) according to the invention are those which contain a combination of the meanings mentioned above as being very especially preferred.

Hydrocarbon radicals such as alkyl or alkenyl—also in connection with hetero atoms such as alkoxy or alkylthio—in the definitions of radicals mentioned hereinabove and hereinbelow are in each case straight-chain or branched as far as this is possible.

If, for example, 5-amino-4-ethoxycarbonyl-3-ethyl-1-methylpyrazole and 4-methoxyphenylacetyl chloride are used as starting materials when preparing compounds of the formula (I) in accordance with process (a), the course of the reaction can be represented by the following equation:

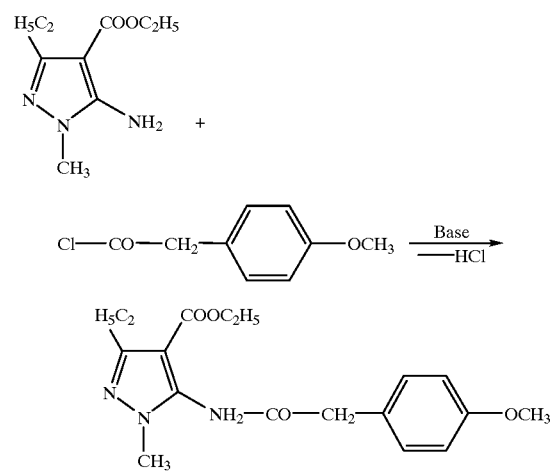

If 5-(4-(4-chlorophenoxy)phenylacetylamino)-3-ethyl-1-methylpyrazole and sulphuryl chloride are used as starting materials when preparing compounds of the formula (I) in accordance with process (b/α), the course of the reaction can be represented by the following equation:

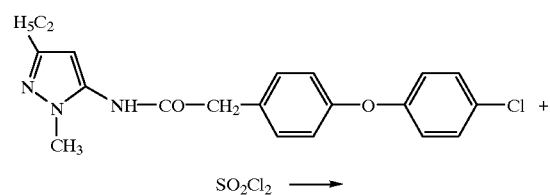

-continued

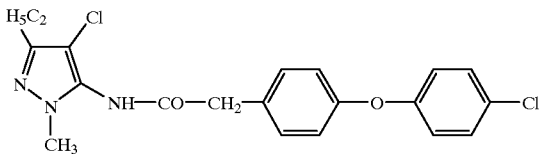

If 5-(4-(4-chlorophenoxy)phenylacetylamino)-3-ethyl-1-methylpyrazole and nitric acid, if appropriate in the presence of acetic acid, are used as starting materials when preparing compounds of the formula (I) in accordance with process (b/β), the course of the reaction can be represented by the following equation:

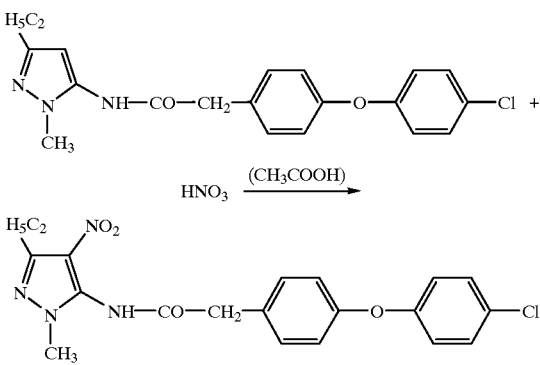

The above-described process (a) for the preparation of compounds of the formula (I) is carried out in the presence of a diluent.

Diluents which can be employed are all customary solvents.

The following can preferably be used: optionally halogenated aliphatic or aromatic hydrocarbons, ethers or nitrites such as, for example, cyclohexane, toluene, chlorobenzene, chloroform, dichloromethane, dichloroethane, dioxane, tetrahydrofuran, diethyl ether or acetonitrile.

The above-described process (a) for the preparation of the compounds of the formula (I) is carried out in the presence of a base.

Bases which can be employed in process (a) are all customary proton acceptors. The following can preferably be used: alkali metal or alkaline earth metal hydroxides, alkali metal or alkaline earth metal carbonates, alkali metal or alkaline earth metal hydrogen carbonates or nitrogen bases. Examples which may be mentioned are sodium hydroxide, calcium hydroxide, potassium carbonate, sodium hydrogen caronate, triethylamine, dibenzylamine, diisopropylamine, pyridine, quinoline, diazabicyclooctane (DABCO), diazabicyclonones (DBN) and diazabicycloundecene (DBU).

The reaction temperatures in the above-described process (a) can be varied within a substantial range. In general, the process is carried out at temperatures between −40° C. and +200° C., preferably between 0° C. and 100° C.

When carrying out the above-described process (a) for the preparation of the compound of the formula (I), 1 to 2 mol, preferably 1 to 1.5 mol, of acid halide of the formula (III) are generally employed per mol of 5-aminopyrazole of the formula (II).

The end products are worked up and isolated in the generally known manner.

The above-described process (b/α) for the preparation of the compounds of the formula (I) is carried out by means of a halogenating agent.

All customary halogenating agents may be employed for this purpose. The following can preferably be used: $Cl_2$, $Br_2$, hypohalous acids or salts thereof such as, for example, sodium hypochlorite, potassium hypochlorite, sodium hypobromite and potassium hypobromite, $SO_2Cl_2$, $S_2Cl_2$, $PCl_5$ or N-bromosuccinimide.

If appropriate, the above-described process (b/α) for the preparation of the compounds of the formula (I) is carried out in the presence of a diluent. The following can preferably be used: optionally halogenated aliphatic or aromatic hydrocarbons, ethers, nitriles or amides such as, for example, cyclohexane, toluene, chlorobenzene, chloroform, dichloromethane, dichloroethane, dioxane, tetrahydrofuran, diethyl ether, acetonitrile or dimethylformamide.

If appropriate, the above-described process (b/α) for the preparation of the compounds of the formula (I) is carried out in the presence of a catalyst. Suitable catalysts which can be employed are all acidic or basic catalysts conventionally used for a halogenation reaction such as, for example, hydrogen halides or sodium acetate, and furthermore free-radical initiators such as azoisobutyronitrile or dibenzoyl peroxide.

When carrying out the above-described process (b/α), the reaction temperatures can be varied within a substantial range. In general, the process is carried out at temperatures between −40° C. and 120° C., preferably between 0° C. and 80° C.

When carrying out the above-described process (b/α) for the preparation of the compounds of the formula (I), 1 to 2 mol, preferably 1 to 1.5 mol, of halogenating agent are generally employed per mol of acylated 5-aminopyrazole of the formula (Ia).

The end products are worked up and isolated in the generally known manner.

The above-described process (b/β) for the preparation of the compounds of the formula (I) is carried out using a nitrating reagent. All customary nitrating reagents can be employed for this purpose. The following can preferably be used: nitric acid, if appropriate in sulphuric acid, water, acetic acid or acetic anhydride, $N_2O_5$ in tetrachloromethane, methyl nitrate together with $BF_3$, sodium nitrite in trifluoroacetic acid or $N_2O_4$.

If appropriate, the above-described process (b/β) for the preparation of the compounds of the formula (I) is carried out in the presence of a diluent. The following can preferably be used: optionally halogenated hydrocarbons such as dichloromethane, chloroform, carbon tetrachloride or chlorobenzene or nitrobenzene.

When carrying out the above-described process (b/β), the reaction temperatures can be varied within a substantial range. In general, the process is carried out at temperatures between 0° C. and 100° C., preferably between 0° C. and 40° C.

When carrying out the above-described process (b/β) for the preparation of the compounds of the formula (I), 1 to 5 mol, preferably 1 to 2 mol, of nitrating reagent are generally employed per mol of acylated 5-aminopyrazole of the formula (Ia).

The end products are worked up and isolated in the generally known manner.

The starting materials of the formula (II) used in preparation process (a) are largely known (cf., for example, J. Org. Chem. 1956, 21, p. 1240 et seq. and 1964, 29, p. 1915 et seq., and J. Chem. Research 1993, p. 76 et seq.) or can be prepared by known methods (cf., for example, the above references).

Hitherto unknown and also a subject of the present invention are 5-aminopyrazoles of the formula (IIa)

(IIa)

[Structure: pyrazole with R¹, Cl, N-R³, NH-R⁴]

in which
R¹, R³ and R⁴ have the abovementioned meaning.

The new 5-aminopyrazoles of the formula (IIa) are obtained by reacting 5-aminopyrazoles of the formula (IV)

(IV)

[Structure: pyrazole with R¹, N-R³, NH-R⁴]

in which
R¹, R³ and R⁴ have the abovementioned meaning
with a chlorinating agent, preferably with sulphuryl chloride, in the presence of aqueous hydrochloric acid in accordance with process (b/α).

The acid halides of the formula (III) furthermore to be used as starting materials in preparation process (a) are generally known compounds of organic chemistry. In formula (III) Hal preferably represents chlorine or bromine.

The starting materials of the formula (Ia) used in preparation process (b) are compounds according to the invention and can be obtained in accordance with the information given in preparation process (a).

Certain acylated 5-aminopyrazoles of the formula (I) can also be obtained when 5-aminopyrazole derivatives of the formula (Ib)

(Ib)

[Structure: pyrazole with R¹, R², N-R³, N(R⁴)-CO-R⁷]

in which
R¹, R², R³ and R⁴ have the abovementioned meaning and
R⁷ represents the group —Y—R⁸ in which
Y has the abovementioned meaning and
R⁸ represents halogenoaryl, preferably iodo- or bromophenyl, especially preferably 4-iodo- or bromophenyl
are reacted with boronic acids of the formula (V)

Ar—B(OH)₂ (V)

in which
Ar represents optionally substituted phenyl, suitable substituents preferably, especially preferably or very especially preferably being those which have already been mentioned in the description of the compounds of the formula (I) as being preferable, especially preferred or very especially preferred substituents for R⁶, in the presence of a base such as, for example, potassium carbonate and in the presence of a diluent such as, for example, toluene, preferably at the boiling point of the solvent used.

If, for example, 5-(4-bromophenylacetyl)amino-4cyano-3-ethyl-1-methylpyrazole and 4-trifluoromethoxyboronic acid are used as starting materials in accordance with this process, the course of the reaction can be represented by the following equation.

[Reaction scheme: C₂H₅/CN pyrazole-NH-CO-CH₂-C₆H₄-Br + (HO)₂B-C₆H₄-OCF₃ → C₂H₅/CN pyrazole-NH-CO-CH₂-C₆H₄-C₆H₄-OCF₃]

The substances of the formula (Ib) are accessible for example by the process according to the invention for the preparation of substances of the formula (I) (cf. the preparation examples).

The compounds of the formula (V) are known and/or can be prepared in a simple manner by known processes.

The active compounds are suitable for controlling animal pests, preferably arthropods, in particular insects and arachnids, which are found in agriculture, in forests, in the protection of stored products and of materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Macrosiphum avenae,* Myzus spp., Phemigus. spp., *Phorodon humuli, Phylloxera vastatrix, Rhopalosiphum padi,* Empoasca spp., *Euscelis bilobatus, Nephotettix cincticeps, Lecanium corni, Saissetia oleae, Laodelphax striatellus, Niraparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis,* Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention are distinguished by potent insecticidal and acaracidal activity.

In particular, compounds of the formula (I) according to the invention are distinguished by an outstanding insecticidal activity. When employed against foliar and soil-dwelling insects, they show a potent activity, for example against mustard beetle lavae (*Phaedon cochleariae*), against caterpillars of the diamond-back moth (*Plutella maculipennis*) and caterpillars of the fall armyworm (*Spodoptera frugiperda*), and against the green rice leafhopper (*Nephotettix cincticeps*).

The active compounds can be converted into the customary formulations, such as solutions, emulsions, suspensions, powders, dusts, pastes, soluble powders, granules, suspoemulsion concentrates, natural and synthetic substances impregnated with active compounds and microencapsulations in polymeric substances.

These formulations are produced in a known manner, for example by mixing the active compounds with extenders, that is, liquid solvents and/or solid carriers, optionally with the use of surfactants, that is, emulsifiers and/or dispersants, and/or foam formers.

In the case of the use of water as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are:

for example ground natural minerals such as kaolins, clays, talc, chalk, quartz, attapulgite, montmorillonite or diatomaceous earth, and ground synthetic minerals such as highly-disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example non-ionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compound according to the invention may be present in its commercially available formulations and in the use forms prepared from these formulations as a mixture with other active compounds such as insecticides, attractants, sterilants, bactericides, acaricides, nematizides, fungicides, growth regulators or herbicides. The insecticides include, for example, phosphoric esters, carbamates, carboxylic esters, chlorinated hydrocarbons, phenyl ureas, substances produced by microorganisms, and others.

Examples of particularly advantageous components in mixtures are the following:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thizole-5-carboxanilide; 2,6-dichloro-N-(4-trifluoromethylbenzyl)benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb; ziram.

Bactericides bronopol, dichlorophen, nitrapyrin, nickel dimethyldithiocarbamate, kasugamycin, octhilinone, furan-carboxylic acid, oxytetracyclin, probenazole, streptomycin, tecloftalam, copper sulphate and other copper preparations.

Insecticides/Acaricides/Nematicides abamectin, acephate, acrinathrin, alanycarb, aldicarb, alphamethrin, amitraz, avermectin, AZ 60541, azadirachtin, azinphos A, azinphos M, azocyclotin, Bacillus thuringiensis, 4-bromo-2-(4-chlorophenyl)-1-(ethoxymethyl)-5-(trifluoromethyl)-1H-pyrrole-3-carbonitrile, bendiocarb, benfuracarb, bensultap, betacyluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chlorethoxyfos, chloretoxyfos, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermnectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamdon, phoxim, pirimicarb, pirimiphos M, pirimiphos A, profenofos, profenophos, promecarb, propaphos, propoxur, prothiofos, prothoate, pymetrozin, pyrachlophos, pyraclofos, pyrachlophos, pyradaphenthion, pyresmethrin, pyrethrum, pyridaben, pyrimidifen, pyriproxifen, quinalphos, salithion, sebufos, silafluofen, sulfotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth regulators are also possible.

Moreover, the active compound according to the invention can be present in its commercially available formulations and in the use forms prepared from these formulations as a mixture with synergists. Synergists are compounds by which the activity of the active compounds is increased without it being necessary for the synergist added to be active itself.

The active compound content of the use forms prepared from the commercially available formulations can vary within wide ranges. The active compound concentration of the use forms can be from 0.0000001 to 95% by weight of active compound, preferably between 0.00001 and 1% by weight.

The use forms are employed in the customary manner which is adapted to suit them.

When used against hygiene and stored-product pests, the active compound is distinguished by an outstanding residual action on wood and clay and by a good stability to alkali on limed substrates.

Furthermore, it has been found that the compounds of the formula I according to the invention have a potent insecticidal activity against insects which destroy industrial materials.

The following insects may be mentioned by way of example and as being preferred, but without limitation:
beetles, such as
*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec. Tryptodendron spec. *Apate monachus, Bostyrchus capucins, Heterobostrychus brunneus,* Sinoxylon spec. *Dinoderus minutus.*

Dermapterans, such as
*Sirex juvencus, Urocerus gigas, Urocerus gigas taignus, Urocerus augur.*

Termites, such as
*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails,
such as *Lepisma saccharina.*

Industrial materials are to be understood as meaning, in the present context, non-live materials such as, preferably, polymers, glues, sizes, papers and boards, leather, wood and derived timber products, and paints.

The material to be protected against attack by insects is very particularly preferably wood and derived timber products.

Wood and derived timber products which can be protected by the agent according to the invention or by compositions comprising it are to be understood as meaning, for example, construction timber, wooden beams, railway sleepers, bridge components, jetties, wooden vehicles, boxes, pallets, containers, telephone poles, wood laggings, windows and doors made of wood, plywood, particle boards, joiner's work, or wood products which are generally used in construction or in joinery.

The active compounds can be used as such, in the form of concentrates or generally customary formulations, such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellent, if appropriate desiccants and UV stabilizers and, if appropriate, colourants and pigments and other processing auxiliaries.

The insecticidal compositions or concentrates used for the protection of wood and timber products comprise the active compound according to the invention in a concentration of 0.0001 to 95% by weight, in particular 0.001 to 60% by weight.

The amount of the agents or concentrates employed depends on the species and the abundance of the insects, and on the medium. The optimum amount used can be determined in each case by test series. However, in general it suffices to employ 0.0001 to 20% by weight, preferably 0.001 to 10% by weight, of the active compound based on the material to be protected.

The solvent and/or diluent used is an organochemical solvent or solvent mixture and/or an oily or oil-like solvent or solvent mixture of low volatility and/or a polar organochemical solvent or solvent mixture and/or water and, if appropriate, an emulsifier and/or wetting agent.

The organochemical solvents employed are preferably oily or oil-like solvents with an evaporation number of above 35 and a flash point of above 30° C., preferably above 45° C. Substances which are used as such oily and oil-like solvent of low volatility which are insoluble in water are suitable mineral oils or their aromatic fractions and mineral-oil-comprising solvent mixtures, preferably white spirit, petroleum and/or alkylbenzene.

It is advantageous to use mineral oils with a boiling range of 170 to 220° C., white spirit with a boiling range of 170 to 220° C., spindle oil with a boiling range of 250 to 350° C., petroleum or aromatics of a boiling range of 160 to 280° C., spirit of turpentine and the like.

In a preferred embodiment, the substances used are liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthaline, preferably α-monochloronaphthaline.

The organic oily or oil-like solvents of low volatility with an evaporation number of above 35 and a flash point of above 30° C., preferably above 45° C., can be replaced in part by organochemical solvents of low or medium volatility, with the proviso that the solvent mixture also has an evaporation number of above 35 and a flash point of above 30° C., preferably above 45° C., and that the insecticide/fungicide mixture is soluble or emulsifiable in this solvent mixture.

In a preferred embodiment, part of the organochemical solvent or solvent mixture or an aliphatic polar organochemical solvent or solvent mixture is replaced. Substances which are preferably used are aliphatic organochemical solvents containing hydroxyl and/or ester and/or ether groups, such as for example, glycol ethers, esters and the like.

Organochemical binders which are used within the scope of the present invention are the binding drying oils and/or synthetic resins which are known per se, can be diluted with water and/or are soluble, dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene-cumaroune resin, silicone resin, drying vegetable and/or drying oils and/or physically drying binders based on a natural and/or synthetic resin.

The synthetic resin used as binder can be employed in the form of an emulsion, dispersion or solution. Substances which can also be used as binders are bitumen or bituminous substances in amounts of up to 10% by weight. In addition, colourants, pigments, water repellants, odoriferous substances and inhibitors or anticorrosives which are known per se can be employed, inter alia.

The composition or concentrate preferably comprises, in accordance with the invention, at least one alkyd resin or modified alkyd resin and/or a drying vegetable oil as the organochemical binder. Substances which are preferably used according to the invention are alkyd resins with an oil content of over 45% by weight, preferably 50 to 68% by weight.

All or some of the abovementioned binder can be replaced by a fixative (mixture) or plasticizer (mixture). These additives are intended to prevent volatilization of the active compounds and crystallization or precipitation. They preferably replace 0.01 to 30% of the binder (based on 100% of binder employed).

They plasticizers are from the chemical classes of the phthalic esters, such as dibutyl phthalate, dioctyl phthalate or benzylbutyl phthalate, the phosphoric esters, such as tributyl phosphate, the adipic esters, such as di(2-ethylhexyl) adipate, the stearates, such as butyl stearate or amyl stearate, the oleates, such as butyl oleate, the glycerol ethers or higher-molecular-weight glycol ethers, glycerol esters and p-toluene sulphonic esters.

Fixatives are based chemically on polyvinyl alkyl ethers such as, for example, polyvinyl methyl ether, or ketones such as benzophenone or ethylene benzophenone.

Another suitable solvent or diluent is, in particular, water, if appropriate in a mixture with one or more of the abovementioned organochemical solvents or diluents, emulsifiers and dispersants.

A particularly effective protection of wood is achieved by means of industrial-scale impregnating processes, for example vacuum, double-vacuum or pressure processes.

If appropriate, the ready-to-use compositions can comprise other insecticides and, if appropriate, also one or more fungicides.

Additional components which may be mixed are preferably the insecticides and fungicides mentioned in WO 94/29 268. The compounds mentioned in the above document are expressly part of the present application.

Components which may very particularly preferably be mixed are insecticides, such as chloropyriphos, phoxim, silafluofin, alphamethrin, cyfluthrin, cypermethrin, deltamethrin, permethrin, imidacloprid, NI-25, flufenoxuron, hexaflumuron and triflumuron, and fungicides such as epoxyconazole, hexaconazole, azaconazole, propiconazole, tebuconazole, cyproconazole, metconazole, imazalil, dichlorfluanid, tolylfluanid, 3-iodo-2-propinyl butylcarbamate, N-octyl-isothiazolin-3-one and 4,5-dichloro-N-octylisothiazolin-3-one.

Preparation and use of the active compounds according to the invention can be seen from the examples which follow.

PREPARATION EXAMPLES

Example 1

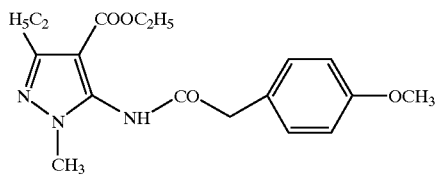

(Process a)

0.47 g (0.006 mol) of pyridine is added at room temperature to a solution 0.99 g (0.005 mol) of 5-amino-4-ethoxycarbonyl-3-ethyl-1-methylpyrazole in 80 ml of dichloromethane. A solution of 1.11 g (0.006 mol) of 4-methoxyphenylacetyl chloride in 20 ml of dichloromethane is subsequently added dropwise at the same temperature. The mixture is stirred overnight at room temperature and subsequently, with reflux, for 24 hours. When cold, the reaction mixture is washed with dilute HCl and with dilute aqueous NaHCO$_3$ solution. The organic phase is dried over MgSO$_4$, filtered and evaporated to dryness.

This gives 1.28 g (74% of theory) of 4-ethoxycarbonyl-3-ethyl-5-(4-methoxyphenylacetyl)amino-1-methylpyrazole as a yellow solid of melting point 112 to 113° C.

Example 2

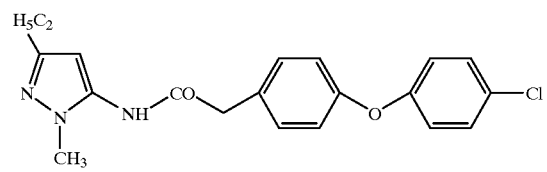

(Process a)

0.95 g (0.012 mol) of pyridine is added at room temperature to a solution of 1.25 g (0.01 mol) of 5-amino-3-ethyl-1-methylpyrazole in 120 ml of dichloromethane. A solution of 3.37 g (0.012 mol) of 4-(4-chlorophenoxy)phenylacetyl chloride in 30 ml of dichloromethane is subsequently added dropwise at the same temperature. After the mixture has been stirred overnight at room temperature, it is washed in succession with dilute HCl and dilute aqueous NaHCO$_3$ solution, and the product is dried over MgSO$_4$, filtered and evaporated to dryness.

This gives 3.10 g (84% of theory) of 5-(4-(4-chlorophenoxy)phenylacetylamino)-3-ethyl-1-methylpyrazole as a brown oil.

$^1$H NMR (CDCl$_3$): δ=1.19, 2.57, 3.56, 3.63, 3.73, 6.04, 6.92–7.03, 7.27–7.33 ppm Example 3

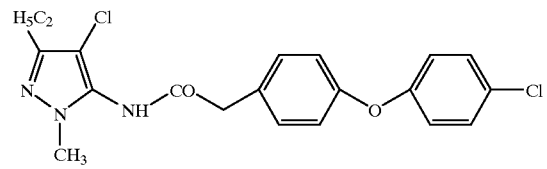

(Process b/α)

0.37 g (0.00275 mol) of sulphuryl chloride are added dropwise at 0° C. to a solution of 0.92 g (0.0025 mol) of 5-(4-(4-chlorophenoxy)phenylacetylamino)-3-ethyl-1-methylpyrazole (Ex. 2) in 10 ml of dichloromethane. After the mixture has been stirred overnight at room temperature, it is diluted with 10 ml of dichloromethane and washed in succession with water, saturated aqueous NaHCO$_3$ solution and saturated aqueous NaCl solution, dried over MgSO$_4$, filtered and evaporated to dryness.

This gives 0.80 g (79% of theory) of 4-chloro-5-(4-(4-chlorophenoxy)phenylacetylamino)-3-ethyl-1-methylpyrazole as a brown oil.

$^1$H NMR (CDCl$_3$): δ=1.21, 2.57, 3.63, 3.77, 6.82, 6.92–7.04, 7.30–7.35 ppm

Example 4

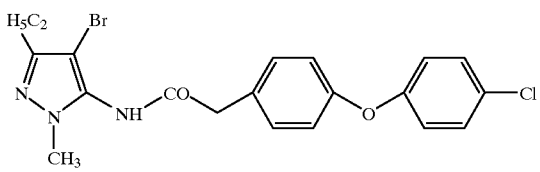

(Process b/α)

0.44 g (0.00275 mol) of bromine are added dropwise at 0° C. to a solution of 0.92 g (0.0025 mol) of 5-(4-(4-chlorophenoxy)phenylacetylamino)-3-ethyl-1-methylpyrazole (Ex. 2) in 10 ml of dichloromethane. After the mixture has been stirred overnight at room temperature, it is diluted with 10 ml of dichloromethane and washed in succession with water, saturated aqueous NaHCO₃ solution and saturated aqueous NaCl solution, dried over MgSO₄, filtered and evaporated to dryness.

This gives 0.90 g (80% of theory) of 4-bromo-5-(4-(4-chlorophenoxy)phenylacetylamino)-3-ethyl-1-methylpyrazole as a brown oil.

$^1$H NMR (CDCl$_3$): δ=1.20, 2.56, 3.66, 3.77, 6.80, 6.91–7.04, 7.27–7.36 ppm

Example 5

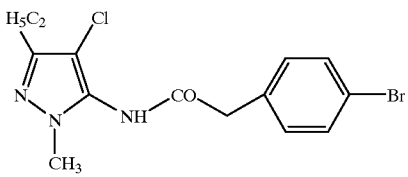

(Process a)

1.90 g (0.024 mol) of pyridine are added at room temperature to a solution of 3.19 g (0.02 mol) of 5-amino-4-chloro-3-ethyl-1-methylpyrazole (Ex. IV-1) in 120 ml of dichloromethane. A solution of 5.60 g (0.024 mol) of 4-bromophenylacetyl chloride in 30 ml of dichloromethane is subsequently added dropwise at the same temperature. The mixture is stirred overnight at room temperature and then washed with dilute HCl and dilute aqueous NaHCO₃ solution. The organic phase is dried over MgSO₄, filtered and evaporated to dryness.

This gives 4.61 g (63% of theory) of 5-(4-bromophenylacetyl)amino4-chloro-3-ethyl-1-methylpyrazole as a colourless solid of melting point 167–168° C.

Preparation of the Starting Materials of Formula (IV)

Example (IV-1)

14.85 g (0.11 mol) of sulphuryl chloride are added dropwise at room temperature to a solution of 12.5 g (0.1 mol) of 5-amino-3-ethyl-1-methylpyrazole in 100 ml of 20% strength HCl. The mixture is stirred for 40 hours at 60° C. After adding 7.43 g (0.055 mol) of sulphuryl chloride, the mixture is stirred for a further 6 hours at 60° C. After adding 2.97 g (0.022 mol) of sulphuryl chloride and stirring for a further 18 hours at 60° C., the mixture is treated with water, the pH is brought to 9 using dilute aqueous NaOH solution, and the mixture is extracted repeatedly with diethyl ether. The combined organic phases are dried over MgSO₄, filtered and evaporated to dryness.

This gives 13.47 g (84% of theory) of 5-amino-4-chloro-3-ethyl-1-methylpyrazole as a pale yellow solid of melting point 50–51° C.

The following compounds of the formula (I) are obtained analogously or following the general preparation instructions:

TABLE 1

(1)

| Ex. No. | $R^1$ | $R^2$ | $R^3$ | $R^4$ | $R^5$ | Melting point or δ (ppm; $^1$H NMR in CDCl$_3$) |
|---|---|---|---|---|---|---|
| 6 | CH$_3$ | CN | CH$_3$ | H | 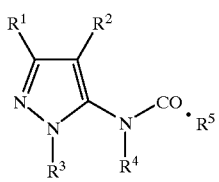 | 1.27; 2.22; 3.34; 3.57*) |

TABLE 1-continued

Structure (1):
Pyrazole with R¹ at 3-position, R² at 4-position, R³ on N1, and at 5-position N(R⁴)-CO-R⁵

| Ex. No. | R¹ | R² | R³ | R⁴ | R⁵ | Melting point or δ (ppm; ¹H NMR in CDCl₃) |
|---|---|---|---|---|---|---|
| 7 | $C_2H_5$ | CN | $CH_3$ | H | —$CH_2$—C₆H₄—t-$C_4H_9$ | 124–127° C. |
| 8 | $C_2H_5$ | CN | $CH_3$ | H | —$CH_2$—C₆H₄—$OCH_3$ | 127–128° C. |
| 9 | $C_2H_5$ | CN | $CH_3$ | H | —$CH_2$—C₆H₄—Cl | 148–151° C. |
| 10 | $C_2H_5$ | CN | $CH_3$ | H | —$CH_2$—C₆H₄—Br | 153–154° C. |
| 11 | $C_2H_5$ | CN | $CH_3$ | H | —$CH_2$—C₆H₃(Cl)(Cl) | 171–173° C. |
| 12 | $C_2H_5$ | CN | $CH_3$ | H | —$CH_2$—C₆H₄—C₆H₄—$OCF_3$ | 152–155° C. |
| 13 | $C_2H_5$ | CN | $CH_3$ | H | —$CH_2$—C₆H₄—O—C₆H₄—Cl | 126–128° C. |
| 14 | $C_2H_5$ | CN | $CH_3$ | H | —$CH_2$—C₆H₄—O—C₆H₄—$OCF_3$ | 1.27; 1.68; 3.62; 3.77 |
| 15 | $C_2H_5$ | CN | $CH_3$ | H | —$CH_2$—C₆H₄—O—C₆H₄—CN | 170–171° C. |
| 16 | $C_2H_5$ | CN | $CH_3$ | H | —$CH_2$—C₆H₄—O—C₆H₄—$NO_2$ | 169–172° C. |
| 17 | $C_2H_5$ | H | $CH_3$ | H | —$CH_2$—C₆H₄—O—C₆H₄—$OCF_3$ | 1.19; 2.57; 3.73; 6.04 |

TABLE 1-continued (1)

| Ex. No. | $R^1$ | $R^2$ | $R^3$ | $R^4$ | $R^5$ | Melting point or δ (ppm); $^1$H NMR in CDCl$_3$) |
|---|---|---|---|---|---|---|
| 18 | $C_2H_5$ | H | $CH_3$ | $C_2H_5$ | —CH$_2$—C$_6$H$_4$—O—C$_6$H$_4$—Cl | 1.13; 1.26; 2.64; 3.37; 3.42; 5.91 |
| 19 | $C_2H_5$ | Cl | $CH_3$ | H | —CH$_2$—C$_6$H$_4$—O—C$_6$H$_4$—OCF$_3$ | 101–103° C. |
| 20 | $C_2H_5$ | Cl | $CH_3$ | $C_2H_5$ | —CH$_2$—C$_6$H$_4$—O—C$_6$H$_4$—Cl | 1.14; 1.28; 2.66 |
| 21 | $C_2H_5$ | Br | $CH_3$ | H | —CH$_2$—C$_6$H$_4$—O—C$_6$H$_4$—OCF$_3$ | 111–112° C. |
| 22 | $C_2H_5$ | Br | $CH_3$ | $C_2H_5$ | —CH$_2$—C$_6$H$_4$—O—C$_6$H$_4$—Cl | 1.15; 1.28; 3.29 |
| 23 | $C_2H_5$ | $NO_2$ | $CH_3$ | H | —CH$_2$—C$_6$H$_4$—O—C$_6$H$_4$—OCF$_3$ | 1.24; 2.89; 3.76; 3.83; 8.48 |
| 24 | $C_2H_5$ | $COOC_2H_5$ | $CH_3$ | H | —CH$_2$—C$_6$H$_4$—t-C$_4$H$_9$ | 1.20; 1.28; 1.32; 2.78; 3.69; 3.75; 4.20 |
| 25 | $C_2H_5$ | $COOC_2H_5$ | $CH_3$ | H | —CH$_2$—C$_6$H$_4$—Cl | 133–135° C. |
| 26 | $C_2H_5$ | $COOC_2H_5$ | $CH_3$ | H | —CH$_2$—C$_6$H$_4$—Br | 1.21; 1.32; 2.76; 3.68; 3.73; 4.25; 8.44 |
| 27 | $C_2H_5$ | $COOC_2H_5$ | $CH_3$ | H | —CH$_2$—C$_6$H$_3$(Cl)(Cl) | 156–158° C. |
| 28 | $C_2H_5$ | $COOC_2H_5$ | $CH_3$ | H | —CH$_2$—C$_6$H$_4$—C$_6$H$_4$—OCF$_3$ | 1.22; 1.35; 2.74; 3.56; 4.28; 5.04 |

TABLE 1-continued

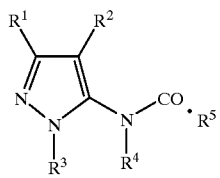

(1)

| Ex. No. | R¹ | R² | R³ | R⁴ | R⁵ | Melting point or δ (ppm; ¹H NMR in CDCl₃) |
|---|---|---|---|---|---|---|
| 29 | C₂H₅ | COOC₂H₅ | CH₃ | H | —CH₂—C₆H₄—O—C₆H₄—Cl | 1.21; 1.32; 2.78; 3.70; 3.76; 4.25 |
| 30 | C₂H₅ | COOC₂H₅ | CH₃ | H | —CH₂—C₆H₄—O—C₆H₄—OCF₃ | 1.21; 1.32; 2.78; 3.71; 3.77; 4.25; 8.48 |
| 31 | C₂H₅ | COOC₂H₅ | CH₃ | H | —CH₂—C₆H₄—O—C₆H₄—CN | 145–147° C. |
| 32 | C₂H₅ | COOC₂H₅ | CH₃ | H | —CH₂—C₆H₄—O—C₆H₄—NO₂ | 114–117° C. |
| 33 | C₂H₅ | Cl | CH₃ | H | —CH₂—C₆H₄—O—C₆H₄—NO₂ | 150–151° C. |
| 34 | C₂H₅ | Cl | CH₃ | H | —CH₂—C₆H₄—O—C₆H₄—CN | 147° C. |
| 35 | C₂H₅ | Cl | CH₃ | H | —CH₂—C₆H₄—C₆H₄—OCF₃ | 147° C. |
| 36 | C₂H₅ | H | CH₃ | H | —CH₂—C₆H₄—O—C₆H₄—CN | 1.20; 2.56; 3.58; 3.76; 6.05 |
| 37 | C₂H₅ | —COOCH₃ | CH₃ | H | —CH₂—C₆H₄—O—C₆H₄—CN | 162° C. |
| 38 | C₂H₅ | —COOCH₃ | CH₃ | H | —CH₂—C₆H₄—O—C₆H₄—NO₂ | 1.21; 2.71; 3.73; 3.78; 3.82 |
| 39 | C₂H₅ | —COOCH₃ | CH₃ | H | —CH₂—C₆H₄—O—C₆H₄—OCF₃ | 1.20; 2.79; 3.71; 3.76; 3.78 |
| 40 | C₂H₅ | Br | CH₃ | H | —CH₂—C₆H₄—O—C₆H₄—CN | 134° C. |

TABLE 1-continued

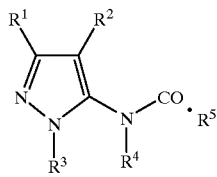

(1)

| Ex. No. | R¹ | R² | R³ | R⁴ | R⁵ | Melting point or δ (ppm; ¹H NMR in CDCl₃) |
|---|---|---|---|---|---|---|
| 41 | $C_2H_5$ | —$COOC_2H_5$ | $CH_3$ | $CH_3$ | —CH₂—C₆H₄—O—C₆H₄—CN | 1.29; 2.90; 3.15; 3.41; 3.43; 4.22 |
| 42 | $C_2H_5$ | —$COOC_2H_5$ | $CH_3$ | $CH_3$ | —CH₂—C₆H₄—O—C₆H₄—$NO_2$ | 1.29; 2.74; 3.16; 3.44; 3.45; 4.22 |
| 43 | $C_2H_5$ | —$COOC_2H_5$ | $CH_3$ | $CH_3$ | —CH₂—C₆H₄—O—C₆H₄—Cl | 1.28; 2.90; 3.13; 3.34; 3.41; 4.20 |
| 44 | $C_2H_5$ | —$COOC_2H_5$ | $CH_3$ | H | —CH₂—C₆H₄—O—C₆H₄—$C_4H_9$-t | 1.32; 2.77; 3.70; 3.75; 4.23; |
| 45 | $C_2H_5$ | CN | $CH_3$ | H | —CH₂—C₆H₄—O—C₆H₄—$C_4H_9$-t | 1.31; 2.67; 3.61; 3.76; |
| 46 | $C_2H_5$ | —$COOC_2H_5$ | $CH_3$ | H | —CH₂—C₆H₄—O—C₆H₄—$NO_2$ | 1.21; 1.33; 2.76; 3.71; 3.80; 4.22 |
| 47 | $C_2H_5$ | CN | $CH_3$ | H | —CH₂—C₆H₄—O—C₆H₄—$NO_2$ | 62–64° C. |
| 48 | $C_2H_5$ | —$COOC_2H_5$ | $CH_3$ | H | —CH₂—C₆H₄—O—C₆H₄—$SCH_3$ | 1.20; 1.30; 2.48; 2.76; 3.70; 3.75; 4.23 |
| 49 | $C_2H_5$ | CN | $CH_3$ | H | —CH₂—C₆H₄—O—C₆H₄—$SCH_3$ | 53–54° C. |
| 50 | $CH_3$ | CN | $CH_3$ | H | —CH₂—C₆H₄—O—C₆H₄—CN | 101° C. |
| 51 | $CH_3$ | CN | $CH_3$ | H | —CH₂—C₆H₄—O—C₆H₄—$NO_2$ | 102–104° C. |

TABLE 1-continued (1)

| Ex. No. | R¹ | R² | R³ | R⁴ | R⁵ | Melting point or δ (ppm; ¹H NMR in CDCl₃) |
|---|---|---|---|---|---|---|
| 52 | $CH_3$ | CN | $CH_3$ | H | —$CH_2$—C₆H₄—O—C₆H₄—Cl | 135–138° C. |
| 53 | $CH_3$ | —$COOC_2H_5$ | $CH_3$ | H | —$CH_2$—C₆H₄—O—C₆H₄—CN | 141–142° C. |
| 54 | $CH_3$ | —$COOC_2H_5$ | $CH_3$ | H | —$CH_2$—C₆H₄—O—C₆H₄—$NO_2$ | 142–144° C. |
| 55 | $CH_3$ | —$COOC_2H_5$ | $CH_3$ | H | —$CH_2$—C₆H₄—O—C₆H₄—Cl | 1.32; 2.36; 3.70; 3.76; 4.25 |
| 56 | $C_2H_5$ | —$COOC_2H_5$ | $CH_3$ | H | —$CH_2$—C₆H₄—O—C₆H₄—$NO_2$ | 1.22; 1.36; 2.80; 3.70; 4.29 |
| 57 | $C_2H_5$ | CN | $CH_3$ | H | —$CH_2$—C₆H₄—O—C₆H₄—$NO_2$ | 62–64° C. |
| 58 | $C_2H_5$ | —$COOC_2H_5$ | $CH_3$ | H | —$CH_2$—C₆H₄—O—C₆H₄—Cl | 1.21; 1.29; 2.76; 3.69; 3.75 |
| 59 | $C_2H_5$ | CN | $CH_3$ | H | —$CH_2$—C₆H₄—O—C₆H₄—Cl | 58–60° C. |
| 60 | $C_2H_5$ | —$COOC_2H_5$ | $CH_3$ | H | —$CH_2$—C₆H₄—O—C₆H₄—$OCF_3$ | 81° C. |
| 61 | $C_2H_5$ | CN | $CH_3$ | H | —$CH_2$—C₆H₄—O—C₆H₄—$OCF_3$ | 133° C. |
| 62 | $C_2H_5$ | —$COOC_3H_7$-i | $CH_3$ | H | —$CH_2$—C₆H₄—O—C₆H₄—CN | 126–128° C. |
| 63 | $C_2H_5$ | —$COOC_3H_7$-i | $CH_3$ | H | —$CH_2$—C₆H₄—O—C₆H₄—$NO_2$ | 82° C. |

TABLE 1-continued (1)

$$\begin{array}{c}R^1\\R^2\\\text{pyrazole ring with N-R}^3, \text{C(=O)R}^5, R^4\end{array}$$

| Ex. No. | $R^1$ | $R^2$ | $R^3$ | $R^4$ | $R^5$ | Melting point or δ (ppm; $^1$H NMR in CDCl$_3$) |
|---|---|---|---|---|---|---|
| 64 | $C_2H_5$ | —COOC$_3$H$_7$-i | CH$_3$ | H | —CH$_2$—C$_6$H$_4$—O—C$_6$H$_4$—OCF$_3$ | 75° C. |
| 65 | $C_2H_5$ | CN | C$_4$H$_9$-t | H | —CH$_2$—C$_6$H$_4$—O—C$_6$H$_4$—CN | 165–167° C. |
| 66 | $C_2H_5$ | —COOC$_2$H$_5$ | CH$_3$ | H | —CH$_2$—C$_6$H$_4$—O—C$_6$H$_3$(F)—CN | 126–128° C. |
| 67 | $C_2H_5$ | CN | CH$_3$ | H | —CH$_2$—C$_6$H$_4$—O—C$_6$H$_3$(F)—CN | 105–107° C. |
| 68 | $C_2H_5$ | —COOC$_2$H$_5$ | C$_4$H$_9$-t | H | —CH$_2$—C$_6$H$_4$—O—C$_6$H$_4$—CN | 184° C. |
| 69 | $C_2H_5$ | —COOC$_2$H$_5$ | C$_4$H$_9$-t | H | —CH$_2$—C$_6$H$_4$—O—C$_6$H$_4$—NO$_2$ | 171° C. |
| 70 | $C_2H_5$ | —COOC$_2$H$_5$ | CH$_3$ | H | —CH$_2$CH$_2$—C$_6$H$_4$—O—C$_6$H$_5$ | 120° C. |
| 71 | $C_2H_5$ | CN | CH$_3$ | H | —CH$_2$CH$_2$—C$_6$H$_4$—O—C$_6$H$_5$ | 178° C. |
| 72 | $C_2H_5$ | —COOC$_2$H$_5$ | CH$_3$ | H | —CH$_2$—C$_6$H$_4$—O—C$_6$H$_3$(F)—NO$_2$ | 131° C. |
| 73 | $C_2H_5$ | CN | CH$_3$ | H | —CH$_2$—C$_6$H$_4$—O—C$_6$H$_3$(F)—NO$_2$ | 163° C. |

TABLE 1-continued (1)

| Ex. No. | $R^1$ | $R^2$ | $R^3$ | $R^4$ | $R^5$ | Melting point or δ (ppm); $^1$H NMR in CDCl$_3$) |
|---|---|---|---|---|---|---|
| 74 | $C_2H_5$ | —COOCH$_2$-CH=CH$_2$ | CH$_3$ | H | —CH$_2$—C$_6$H$_4$—O—C$_6$H$_4$—CN | 121° C. |
| 75 | $C_2H_5$ | —COOCH$_2$-CH=CH$_2$ | CH$_3$ | H | —CH$_2$—C$_6$H$_4$—O—C$_6$H$_4$—NO$_2$ | 1.22; 2.79; 3.73; 3.81; |
| 76 | $C_2H_5$ | —COOC$_2$H$_5$ | $C_3H_7$-i | H | —CH$_2$—C$_6$H$_4$—O—C$_6$H$_4$—CN | 125–127° C. |
| 77 | $C_2H_5$ | —COOC$_2$H$_5$ | $C_3H_7$-i | H | —CH$_2$—C$_6$H$_4$—O—C$_6$H$_4$—NO$_2$ | 124° C. |
| 78 | $C_2H_5$ | CN | $C_3H_7$-i | H | —CH$_2$—C$_6$H$_4$—O—C$_6$H$_4$—CN | 168° C. |
| 79 | $C_2H_5$ | CN | $C_3H_7$-i | H | —CH$_2$—C$_6$H$_4$—O—C$_6$H$_4$—NO$_2$ | 190–192° C. |
| 80 | $C_4H_9$-t | H | CH$_3$ | H | —CH$_2$—C$_6$H$_4$—O—C$_6$H$_4$—CN | 70–71° C. |
| 81 | $C_2H_5$ | —COOC$_2$H$_5$ | CH$_3$ | H | —CH$_2$—C$_6$H$_4$—O—C$_6$H$_2$F$_2$—CN | 186–187° C. |
| 82 | $C_2H_5$ | CN | CH$_3$ | H | —CH$_2$—C$_6$H$_4$—O—C$_6$H$_2$F$_2$—CN | 168° C. |
| 83 | $C_4H_9$-t | Br | CH$_3$ | H | —CH$_2$—C$_6$H$_4$—O—C$_6$H$_4$—CN | 95° C. |

TABLE 1-continued (1)

| Ex. No. | R¹ | R² | R³ | R⁴ | R⁵ | Melting point or δ (ppm; ¹H NMR in CDCl₃) |
|---|---|---|---|---|---|---|
| 84 | $C_4H_9$-t | Cl | $CH_3$ | H | —CH₂—C₆H₄—O—C₆H₄—CN | 1.34; 3.65; 3.81 |
| 85 | $C_2H_5$ | —$COOC_2H_5$ | $CH_3$ | H | —CH₂O—C₆H₄—O—C₆H₄—CN | 85° C. |
| 86 | $C_2H_5$ | CN | $CH_3$ | H | —CH₂O—C₆H₄—O—C₆H₄—CN | 110–111° C. |
| 87 | $C_2H_5$ | —$COOC_2H_5$ | $CH_3$ | H | —CH₂—C₆H₄—O—C₆H₄—SCF₃ | 1.21; 1.33; 2.79; 3.72; 3.79 |
| 88 | $C_2H_5$ | CN | $CH_3$ | H | —CH₂—C₆H₄—O—C₆H₄—SCF₃ | 1.25; 2.67; 3.63; 3.79 |

Use Examples

Example A

Phaedon Larvae Test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and populated with mustard beetle larvae (*Phaedon cochleariae*), while the leaves are still moist.

After the desired period of time, the destruction in % is determined. 100% means that all the beetle larvae have been killed; 0% means that none of the beetle larvae have been killed.

In this test, a destruction of 100% is caused, after 7 days, for example by the compounds of Preparation Examples 2, 3, 9, 10, 11, 12, 13, 15, 16, 29, 31 and 32 at an exemplary active compound concentration of 0.1%.

Example B

Plutella Test
Solvent: 7 parts by weight of dimethylformamide
Emulsifier: 1 part by weight of alkylaryl polyglycol ether To produce a suitable preparation of active compond, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and populated with caterpillars of the diamond-back moth *Plutella maculipennis* while the leaves are still moist.

After the desired period of time, the destruction in % is determined. 100% means that all the caterpillars have been killed; 0% means that none of the caterpillars have been killed.

In this test, a destruction of 100% is caused, after 7 days, for example by the compounds of Preparation Examples 2, 3, 12, 13, 15, 16, 29, 31 and 32 at an exemplary active compound concentration of 0.1%.

Example C

Spodoptera Test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and populated with caterpillars of the fall armyworm (*Spodoptera frugiperda*), while the leaves are still moist.

After the desired period of time, the destruction in % is determined. 100% means that all the caterpillars have been killed; 0% means that none of the caterpillars have been killed.

In this test, a destruction of 100% is caused, after 7 days, for example by the compounds of Preparation Examples 2, 6, 13, 15, 16, 31 and 32 at an exemplary active compound concentration of 0.1%.

Example D

Nephotettix Test

Solvent: 7 parts by weight of dimethylformamide
Emulsifier: 1 part by weight of alkylaryl polyglycol ether To produce a suitable preparation of active compond, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and populated with caterpillars of the green rice leafhopper (*Nephotettix cincticeps*) while the leaves are still moist.

After the desired period of time, the destruction in % is determined. 100% means that all the leafhoppers have been killed; 0% means that none of the leafhoppers have been killed.

In this test, a destruction of at least 90% was caused, after 6 days, for example by the compounds of Preparation Examples 13, 29, 31 and 32 at an exemplary active compound concentration of 0.1%.

What is claimed is:

1. Compounds of the formula (I)

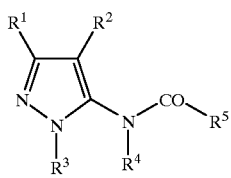

(I)

in which $R^1$ represents alkyl, alkoxyalkyl or halogenoalkyl, $R^2$ represents halogen, cyano, nitro, halogenoalkylthio, alkoxycarbonyl or alkenyloxycarbonyl, $R^3$ represents alkyl or optionally substituted cycloalkyl, $R^4$ represents hydrogen, alkyl or optionally substituted cycloalkyl and $R^5$ represents the group —Y—$R^6$, wherein Y represents $C_1$–$C_4$-alkanediyl, which is optionally substituted by halogen or $C_3$–$C_6$-cycloalkyl and $R^6$ represents phenyl, which is optionally mono-substituted to tri-substituted by identical or different substituents selected from the group consisting of halogen, nitro, cyano, $C_1$–$C_{12}$-alkyl, $C_1$–$C_{12}$-alkoxy and $C_1$–$C_{12}$-alkylthio.

2. Compounds of the formula (I) according to claim 1 in which $R^1$ represents $C_1$–$C_4$-alkyl, $C_1$–$C_4$-alkoxy-$C_1$–$C_4$-alkyl or $C_1$–$C_4$-halogenoalkyl, $R^2$ represents halogen, cyano, nitro, trifluoromethylthio, difluoromethylthio, $C_1$–$C_4$-alkoxy-carbonyl or $C_2$–$C_4$-alkenyloxycarbonyl, $R^3$ represents $C_1$–$C_4$-alkyl, or represents $C_3$–$C_6$-cycloalkyl which is optionally substituted by halogen or $C_1$–$C_4$-alkyl, $R^4$ represents hydrogen, $C_1$–$C_4$-alkyl, or represents $C_3$–$C_6$-cycloalkyl which is optionally substituted by halogen or $C_1$–$C_4$-alkyl, $R^5$ represents the group —Y—$R^6$ wherein Y represents $C_1$–$C_4$-alkanediyl, which is optionally substituted by halogen or $C_3$–$C_6$-cycloalkyl and $R^6$ represents phenyl, which is optionally mono-substituted to tri-substituted by identical or different substituents selected from the group consisting of halogen, nitro, cyano, $C_1$–$C_{12}$-alkyl, $C_1$–$C_{12}$-alkoxy and $C_1$–$C_{12}$-alkylthio.

3. Compounds of the formula (I) according to claim 1, in which $R^1$ represents methyl, ethyl, n- or i-propyl or n-, i-, s- or t-butyl; or represents methoxymethyl, ethoxymethyl, methoxyethyl, ethoxyethyl, trifluoromethyl, difloromethyl, fluoromethyl, 1-chloro-1-ethyl or 1-fluoro-1-ethyl, $R^2$ represents fluorine, chlorine, bromine, cyano, nitro, trifluoromethylthio, difluoromethylthio, methoxycarbonyl, ethoxycarbonyl, n- or i-propoxycarbonyl, n-, i-, s- or t-butoxycarbonyl or allyloxycarbonyl, $R^3$ represents methyl, ethyl, n- or i-propyl, n-, i-, s- or t-butyl, or represents -cyclopropyl, cyclopentyl or cyclohexyl, each of which is optionally substituted by fluorine, chlorine, methyl and/or ethyl, $R^4$ represents hydrogen, methyl, ethyl, n- or i-propyl, n-, i-, s- or t-butyl, or represents cyclopropyl, cyclopentyl or cyclohexyl, each of which is optionally substituted by fluorine, chlorine, methyl and/or ethyl, $R^5$ represents the group —Y—$R^6$, wherein Y represents $C_1$–$C_4$-alkanediyl, which is optionally substituted by halogen or $C_3$–$C_6$-cycloalkyl and $R^6$ represents phenyl, which is optionally mono-substituted to tri-substituted by identical or different substituents selected from the group consisting of halogen, nitro, cyano, $C_1$–$C_{12}$-alkyl, $C_1$–$C_{12}$-alkoxy and $C_1$–$C_{12}$-alkylthio.

4. Compounds of the formula (I) according to claim 1 in which $R^1$ represents methyl, ethyl, i-propyl, t-butyl, methoxymethyl, 1-chloro-1-ethyl or 1-fluoro-1-ethyl, $R^2$ represents chlorine, bromine, cyano, nitro, methoxycarbonyl, ethoxycarbonyl, isopropoxycarbonyl or allyloxycarbonyl, $R^3$ represents methyl, ethyl, i-propyl, t-butyl, or cyclopropyl, $R^4$ represents hydrogen, methyl, ethyl, i-propyl or cyclopropyl, $R^5$ represents the group —Y—$R^6$, wherein Y represents $C_1$–$C_4$-alkanediyl, which is optionally substituted by halogen or $C_3$–$C_6$-cycloalkyl and $R^6$ represents phenyl, which is optionally mono-substituted to tri-substituted by identical or different substituents selected from the group consisting of halogen nitro, cyano, $C_1$–$C_{12}$-alkyl, $C_1$–$C_{12}$-alkoxy and $C_1$–$C_{12}$-alkylthio.

5. Process for the preparation of compounds of the formula (I) according to claim 1, wherein a) 5-aminopyrazoles of the formula (II)

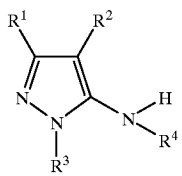
(II)

in which

R$^1$, R$^2$, R$^3$ and R$^4$ have the meaning given in claim 1 are reacted with acid halides of the formula (III)

(III)

in which

R$^5$ has the meaning given in claim 1 and

Hal represents halogen in the presence of a base and in the presence of a diluent; or b) acylated 5-aminopyrazoles of the formula (Ia)

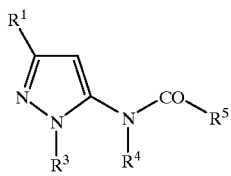
(Ia)

in which

R$^1$, R$^3$, R$^4$ and R$^5$ have the abovementioned meaning are reacted (α) with a halogenating agent, if appropriate in the presence of a diluent and if appropriate in the presence of a catalyst, or (β) with a nitrating agent, if appropriate in the presence of a diluent.

6. A pestical composition comprising a pesticidally effective amount of a compound according to claim 1 and a diluent.

7. A method of combatting unwanted pests which comprises administering to such pests or to a locus from which it is desired to exclude such pests a pesticidally effective amount of a compound according to claim 1.

8. A compound of the formula (I)

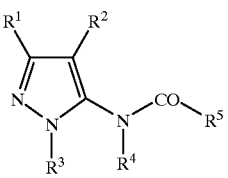
(I)

in which

| R$^1$ | R$^2$ | R$^3$ | R$^4$ | R$^5$ |
|-------|-------|-------|-------|-------|
| CH$_3$ | CN | CH$_3$ | H | —CH$_2$—C$_6$H$_4$—t-C$_4$H$_9$ |

* * * * *